(12) United States Patent
Yasui et al.

(10) Patent No.: US 9,891,240 B2
(45) Date of Patent: Feb. 13, 2018

(54) AUTOMATIC ANALYZER

(71) Applicant: Hitachi High-Technologies Corporation, Tokyo (JP)

(72) Inventors: Akihiro Yasui, Tokyo (JP); Hitoshi Tokieda, Tokyo (JP); Toshihide Orihashi, Tokyo (JP); Yoshiaki Saito, Tokyo (JP); Naoto Suzuki, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 137 days.

(21) Appl. No.: 14/418,614

(22) PCT Filed: Jul. 25, 2013

(86) PCT No.: PCT/JP2013/070215
§ 371 (c)(1),
(2) Date: Jan. 30, 2015

(87) PCT Pub. No.: WO2014/021195
PCT Pub. Date: Feb. 6, 2014

(65) Prior Publication Data
US 2015/0204895 A1   Jul. 23, 2015

(30) Foreign Application Priority Data
Aug. 2, 2012 (JP) ................. 2012-171677

(51) Int. Cl.
*G01N 35/02* (2006.01)
*G01N 35/00* (2006.01)
*G01N 35/10* (2006.01)

(52) U.S. Cl.
CPC ..... *G01N 35/025* (2013.01); *G01N 35/00584* (2013.01); *G01N 35/1004* (2013.01)

(58) Field of Classification Search
CPC ............. G01N 35/1004; G01N 35/025; G01N 35/00584
See application file for complete search history.

(56) References Cited

U.S. PATENT DOCUMENTS 5,474,744 A * 12/1995 Lerch ................. G01N 35/1004
134/169 R
6,003,531 A * 12/1999 Kimura .............. G01N 35/1004
134/155
(Continued)

FOREIGN PATENT DOCUMENTS

| DE | 10207499 A1 * | 9/2003 | ............... B08B 3/02 |
| EP | 2 037 283 A1 | 3/2009 | |

(Continued)

OTHER PUBLICATIONS

International Preliminary Report on Patentability for International Application No. PCT/JP2013/070215 dated Feb. 12, 2015.
(Continued)

*Primary Examiner* — Sean E Conley
*Assistant Examiner* — Benjamin R Whatley
(74) *Attorney, Agent, or Firm* — Mattingly & Malur, PC

(57) ABSTRACT

An automatic analyzer is capable of ensuring sufficient nozzle cleaning and suppressing of deterioration in the accuracy of analysis. When it is judged that there remains no analysis item of the sample, a judgment is made on whether the sample dispensation quantity of the n-th sample dispensation is less than a dispensation quantity threshold value or not, and if less, a cleaning pattern is selected by making a judgment on whether or not all the sample dispensation quantities of the first through (n−1)-th sample dispensations are less than the dispensation quantity threshold value. If the sample dispensation quantity of the n-th sample dispensation is the dispensation quantity threshold value or more, another cleaning pattern selected by making the judgment on
(Continued)

whether or not all the sample dispensation quantities of the first through (n−1)-th sample dispensations are less than the dispensation quantity threshold value.

5 Claims, 9 Drawing Sheets

(56) References Cited

U.S. PATENT DOCUMENTS

| | | | |
|---|---|---|---|
| 2003/0223472 A1* | 12/2003 | Ravalico | G01N 35/1004 374/31 |
| 2007/0175284 A1* | 8/2007 | Oonuma | G01N 35/1004 73/864.21 |
| 2010/0151578 A1 | 6/2010 | Ravalico et al. | |
| 2012/0003731 A1* | 1/2012 | Kuroda | G01N 35/00732 435/288.7 |
| 2014/0286824 A1* | 9/2014 | Yasui | G01N 35/1002 422/64 |

FOREIGN PATENT DOCUMENTS

| | | | |
|---|---|---|---|
| JP | 2010060550 | | 3/2010 |
| JP | 2010060550 A * | | 3/2010 |
| JP | 2011220928 | | 11/2011 |
| WO | WO 2013058170 A1 * | 4/2013 | G01N 35/1002 |

OTHER PUBLICATIONS

Extended European Search Report received in corresponding European Application No. 13825221.8 dated Mar. 7, 2016.

* cited by examiner

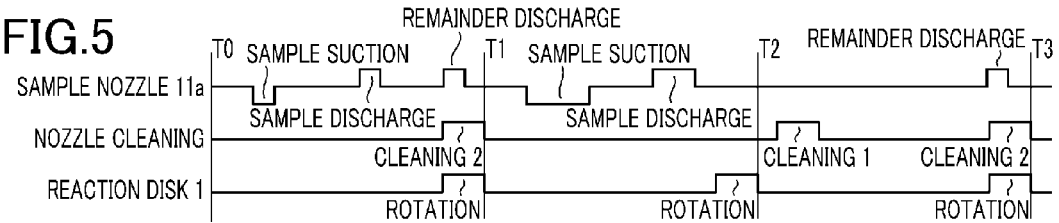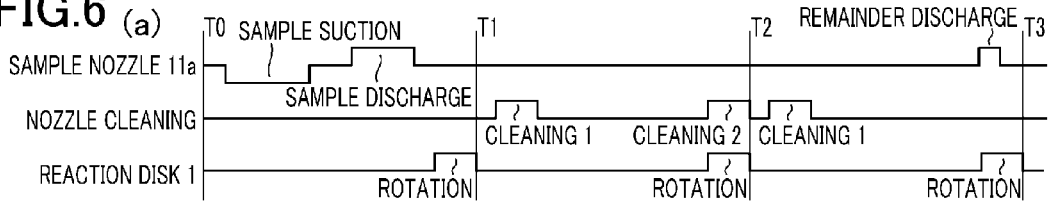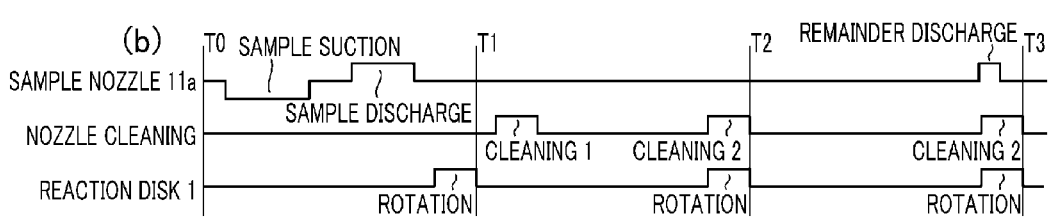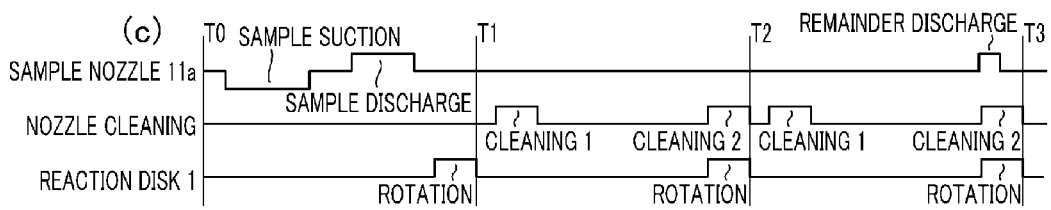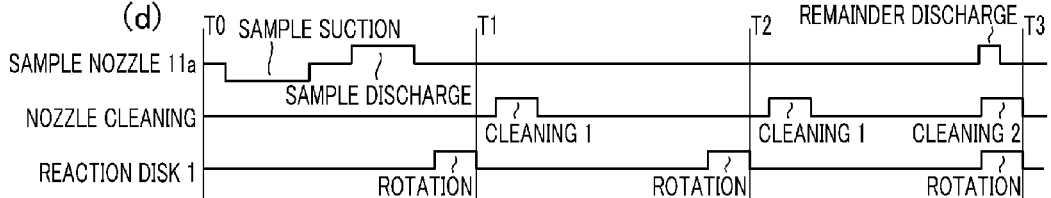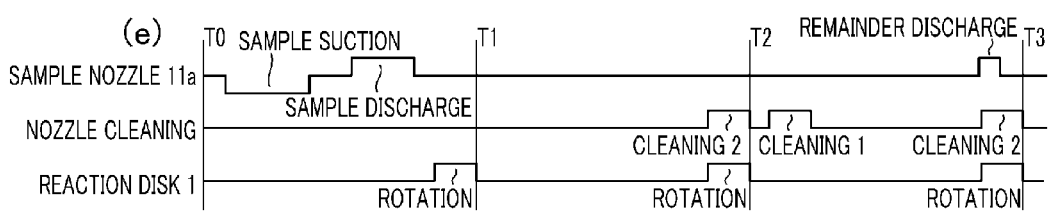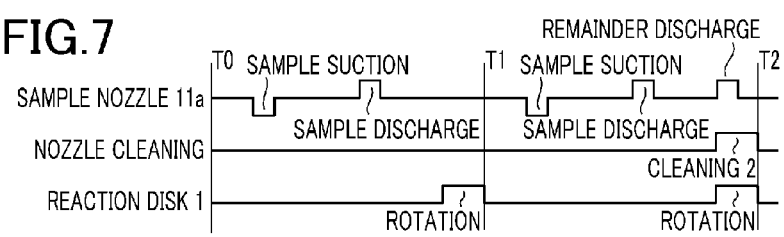

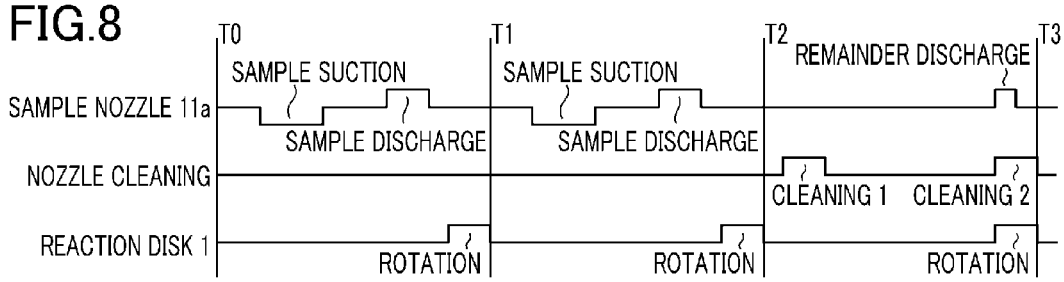
FIG.8
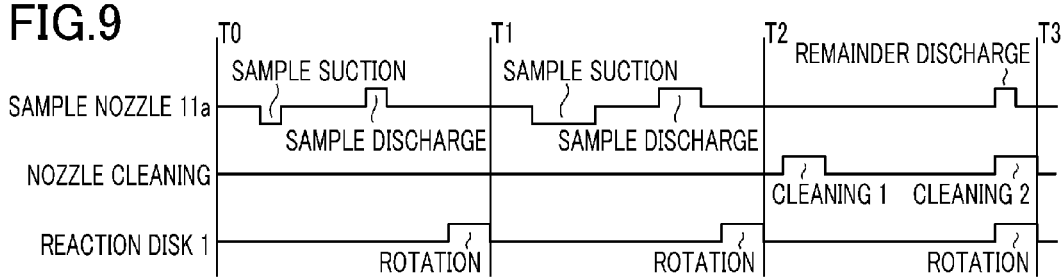
FIG.9
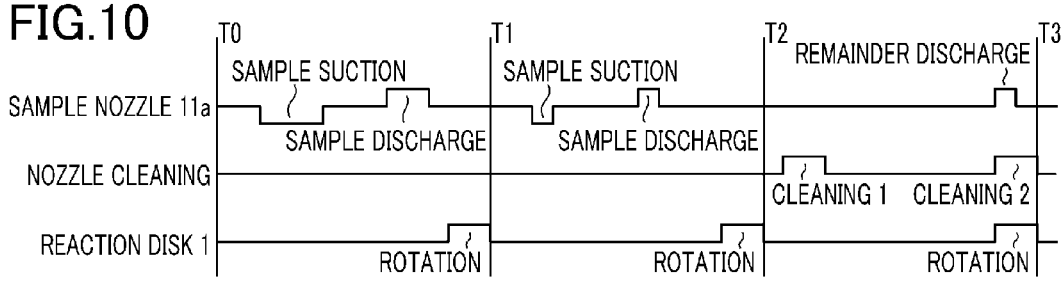
FIG.10
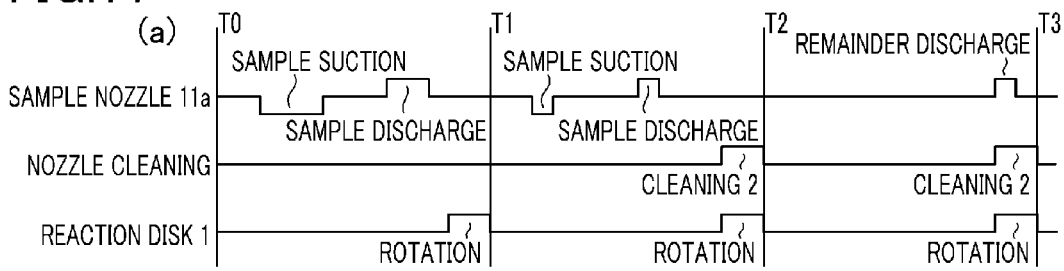
FIG.11 (a)
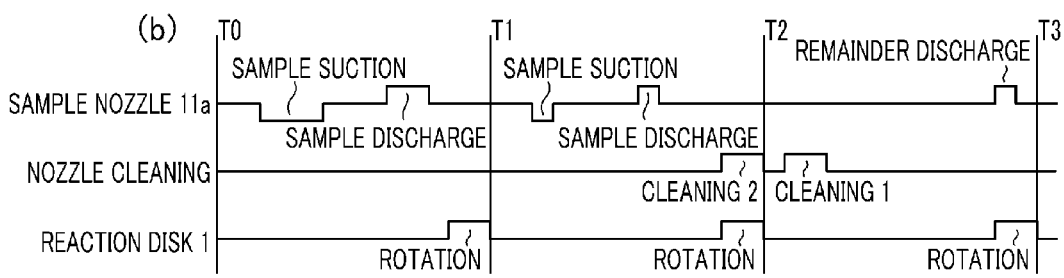
(b)

AUTOMATIC ANALYZER

TECHNICAL FIELD

The present invention relates to an automatic analyzer for conducting quantitative or qualitative analyses of components of blood, urine, etc.

BACKGROUND ART

Automatic analyzers for conducting quantitative or qualitative analyses of particular components contained in a biological sample (blood, urine, etc.) have become indispensable for diagnosis today because of high reproducibility of analysis result, high processing speed, and so forth.

Measurement methods employed by the automatic analyzers are roughly classified into two types: an analysis method using a reagent that reacts with analysis-target constituents in the sample and thereby changes the color of the reaction solution (colorimetric analysis) and an analysis method using a reagent made by adding markers to substances that specifically react directly or indirectly with the analysis-target constituents and counting the number of the markers (immunity analysis). While the analysis in either analysis method is performed by mixing a prescribed amount of reagent into the sample, the mixture ratio between the sample and the reagent varies depending on the analysis item (analytical assay) and a relatively large sample suction (pipetting) quantity from approximately 1 µL to over 20 µL is necessary.

Generally, the automatic analyzer analyzes different samples for a plurality of analysis items. Thus the sample dispensation nozzle (for dispensing the samples) is cleaned for a period between the end of the pipetting of a sample and the start of the pipetting of the next sample and the carry-over between samples is prevented, whereby deterioration in the accuracy of the analysis is reduced.

Further, the automatic analyzer carries out the analysis by programming the sample dispensation and the cleaning in one operation cycle and repeating such an operation cycle. The contaminated region in the nozzle increases especially when the sample suction quantity (quantity of the sample sucked into the nozzle) is large. Thus, in order to sufficiently perform the nozzle cleaning, Patent Document 1 describes a method in which the nozzle cleaning time (duration) is changed based on the type or the dispensation quantity of the sample.

PRIOR ART DOCUMENT

Patent Document

Patent Document 1: JP-2011-220928-A

SUMMARY OF THE INVENTION

Problem to be Solved by the Invention

Improvement in the processing power of the automatic analyzers is being increasingly required in recent years. For example, when high-speed processing of 1000 tests per hour or higher is required, the operation time per operation cycle has to be reduced to 3.6 seconds or less.

On the other hand, the sample suction quantity varies over a wide range (e.g., approximately between 1.0 µL and 35 µL), and thus it is difficult to secure the sample dispensation time and a sufficient nozzle cleaning time in one operation cycle.

In cases where the nozzle cleaning time (duration) is changed based on the type or the dispensation quantity of the sample as in the technique described in the Patent Document 1, an attempt to carry out the aforementioned high-speed processing leads to impossibility of securing a sufficient nozzle cleaning time in one operation cycle since the maximum cleaning time possible in one operation cycle is shortened by the high-speed processing. Consequently, the carry-over between samples can occur.

It is therefore the object of the present invention to implement an automatic analyzer capable of ensuring sufficient nozzle cleaning and suppressing the deterioration in the accuracy of the analysis even when the processing of the sample is speeded up.

Means for Solving the Problem

In order to achieve the above object, the present invention is configured as follows:

An automatic analyzer in accordance with the present invention comprises: a sample dispensation mechanism including a sample nozzle which sucks in a sample stored in a sample vessel and discharges the sample into a reaction vessel; a reagent dispensation mechanism which sucks in a reagent stored in a reagent vessel and discharges the reagent into the reaction vessel; a cleaning mechanism which cleans the sample dispensation nozzle with cleaning water; an analysis unit which analyzes the sample in the reaction vessel; and a controller which controls the operation of the sample dispensation mechanism, the reagent dispensation mechanism, the cleaning mechanism and the analysis unit according to a constant operation cycle. The controller controls a cleaning operation for cleaning the sample dispensation nozzle by setting the number of times and timing of the cleaning of the sample dispensation nozzle by the cleaning mechanism based on maximum sample suction quantity of the sample dispensation nozzle in the first through (N−1)-th sample suction processes and sample suction quantity of the sample dispensation nozzle in the N-th sample suction process in cases where the sample suction is performed N times (N: integer larger than 1) from the same sample.

Effect of the Invention

According to the present invention, it becomes possible to implement an automatic analyzer capable of ensuring sufficient nozzle cleaning and suppressing the deterioration in the accuracy of the analysis even when the processing of the sample is speeded up.

BRIEF DESCRIPTION OF THE DRAWINGS

FIG. 5 is a drawing showing a cleaning method according to an embodiment of the present invention.

FIGS. 6(a)-6(e) are diagrams for explaining the operation in a case where a second threshold value is set in addition to a first threshold value in an embodiment of the present invention.

FIG. 7 is a drawing showing an example in which the sample suction/discharge was performed from one sample in a first embodiment of the present invention.

FIG. 8 is a drawing showing another example in which the sample suction/discharge was performed from one sample in the first embodiment of the present invention.

FIG. 9 is a drawing showing another example in which the sample suction/discharge was performed from one sample in the first embodiment of the present invention.

FIG. 10 is a drawing showing another example in which the sample suction/discharge was performed from one sample in the first embodiment of the present invention.

FIGS. 11(a)-11(b) are diagrams showing another example in which the sample suction/discharge was performed from one sample in the first embodiment of the present invention.

MODE FOR CARRYING OUT THE INVENTION

Figure 1:
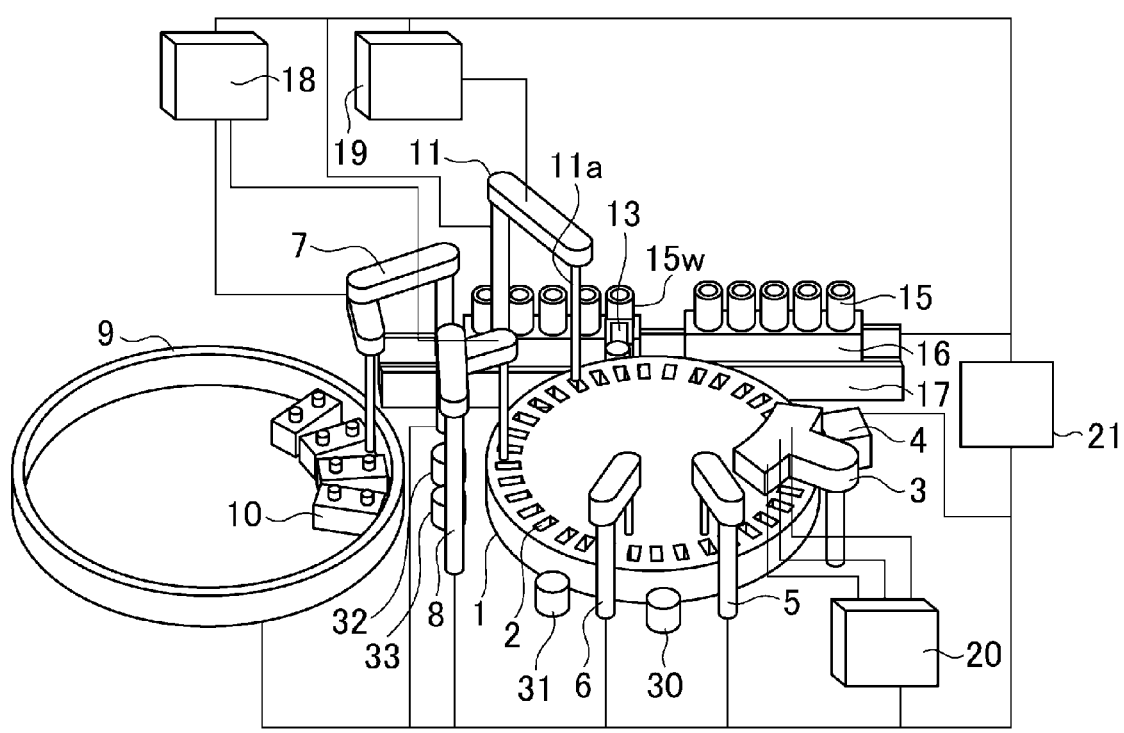
FIG. 1 is a schematic diagram showing the overall configuration of an automatic analyzer to which the present invention is applied.

Referring now to the drawings, a description will be given in detail of preferred embodiments of the present invention.

EMBODIMENTS

First Embodiment

FIG. 1 is a schematic diagram showing the overall configuration of an automatic analyzer to which the present invention is applied.

In FIG. 1, a plurality of reaction vessels 2 are arranged circumferentially on a reaction disk 1. In a reagent disk 9, a plurality of reagent bottles 10 can be arranged along a circle. A sample transfer mechanism 17 for moving a rack 16 holding sample vessels 15 is provided in the vicinity of the reaction disk 1. Arranged between the reaction disk 1 and the reagent disk 9 are reagent dispensation mechanisms 7 and 8 for sucking in a reagent from a reagent bottle 10 and discharging the reagent into a reaction vessel 2.

A sample dispensation mechanism 11 capable of rotating and moving up and down is provided between the reaction disk 1 and the sample transfer mechanism 17. The sample dispensation mechanism 11 has a sample dispensation nozzle 11a (hereinafter abbreviated as a "sample nozzle 11a"). A sample pump 19 is connected to the sample nozzle 11a. The sample nozzle 11a moves along an arc around the rotation axis of the sample dispensation mechanism 11 and dispenses a sample (sample dispensation) by sucking in the sample from a sample vessel 15 and discharging the sample into a reaction vessel 2.

Arranged around the reaction disk 1 are the reaction vessels 2, a cleaning mechanism 3, a spectrophotometer 4, stirring mechanisms 5 and 6, the reagent disk 9, and the sample transfer mechanism 17. A cleaning pump 20 is connected to the cleaning mechanism 3. Cleaning baths 13, 30, 31, 32 and 33 are placed respectively in the operation ranges of the reagent dispensation mechanism 7, the reagent dispensation mechanism 8, the sample dispensation mechanism 11, the stirring mechanism 5 and the stirring mechanism 6. A reagent pump 18 is connected to the reagent dispensation mechanisms 7 and 8.

Each sample vessel 15 contains a sample (e.g., blood) to be inspected (test sample), is set on the rack 16 and transferred by the sample transfer mechanism 17. The sample dispensation mechanism 11 sucks in a sample from a sample vessel 15 that is situated at a sample suction position 15w. The mechanisms explained above are connected to a controller 21 and the operation of the mechanisms is controlled by the controller 21. The controller 21 also has a function of an analysis unit for analyzing the test sample in each reaction vessel 2.

Figure 2:
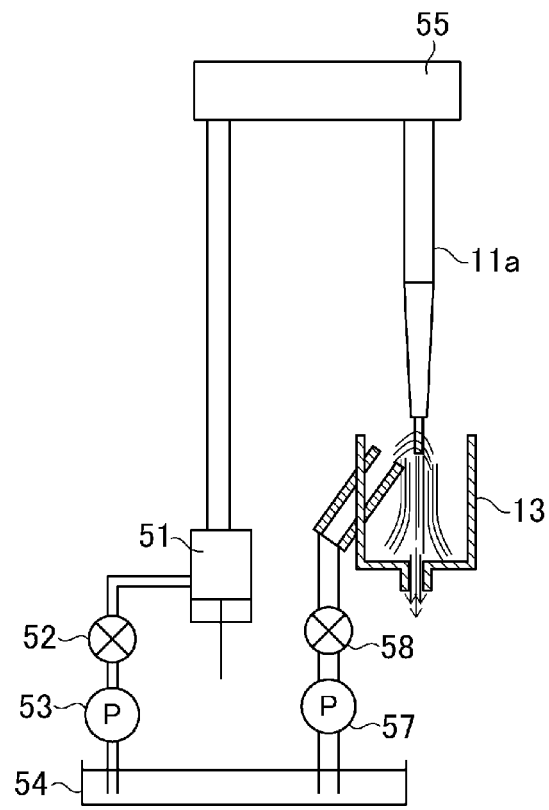
FIG. 2 is a schematic diagram showing the overall configuration of a sample dispensation mechanism in an embodiment of the present invention.

FIG. 2 is a schematic diagram showing the overall configuration of the sample dispensation mechanism 11 in an embodiment of the present invention. In FIG. 2, the sample nozzle 11a for sucking in and discharging a sample can be moved up and down and rotated by an arm 55. The nozzle 11a is connected to a pipetter 51 which generates differential pressure for causing the sample to flow in the channel. The nozzle 11a is equipped with a pump 53 for supplying system water to a channel that extends from the pipetter 51 to the nozzle 11a, a channel connecting the pump 53 to the pipetter 51, and at least one solenoid valve 52 arranged in the channel to control the flow of the system water. Cleaning water is stored in a tank 54.

The cleaning bath 13 for the cleaning of the sample nozzle 11a is equipped with a pump 57 for supplying the cleaning water from the tank 54, a channel connecting the pump 57 and the cleaning bath 13, and a solenoid valve 58 arranged in the channel to control the flow of the cleaning water. Cleaning water is stored in a tank 54.

Figure 3:
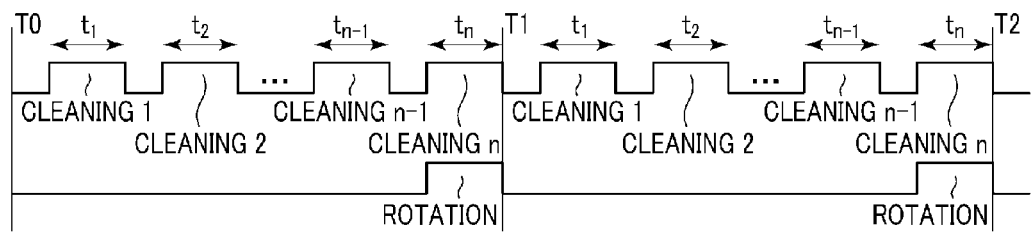
FIG. 3 is a drawing showing an example of the setting of nozzle cleaning timing possible in one operation cycle in an embodiment of the present invention.

FIG. 3 shows an example of the setting of cleaning timing of the nozzle 11a possible in one operation cycle (T0-T1 or T1-T2) in an embodiment of the present invention. The length of one cycle is the same as that of the rotation cycle of the reaction disk. In the present invention, one operation cycle includes a plurality of time points (periods) at/in which the nozzle cleaning is possible, from which one or more cleaning time points (cleaning periods) are selected (as the cleaning timing) depending on the dispensation quantity of the dispensation nozzle 11a.

Incidentally, cleaning times (durations) $t_1$-$t_n$ of the cleaning time points (cleaning periods) may either be the same or different from each other. When the pump 57 is used also for the cleaning of reagent nozzles of the reagent dispensation mechanisms 7 and 8, it is desirable that the cleaning execution periods of the sample nozzle 11a and the cleaning execution periods of the reagent nozzles of the reagent dispensation mechanisms 7 and 8 do not overlap with each other. In cases where the cleaning execution periods of the sample nozzle 11a and those of the reagent nozzles overlap with each other, it is desirable to properly control and stabilize the amount of the cleaning water used for the reagent nozzles by fixing the nozzle cleaning execution points (periods) and the cleaning times (durations) $t_1$-$t_n$.

In the cleaning of the nozzle 11a, simply extending the cleaning time as mentioned above is not a good idea. If the total cleaning time is constant, separating the cleaning into multiple cleaning processes (periods) is better. When the cleaning is separated into two cleaning processes, for example, it is possible to replace the sample in the nozzle 11a with the cleaning water in the first cleaning process. Stains remaining on the inner wall of the nozzle 11a diffuse into the cleaning water (which replaced the sample in the first cleaning process) until the start of the second cleaning process, and thus the stains can be removed more by the second cleaning process. Consequently, the cleaning efficiency can be increased.

Figure 4:
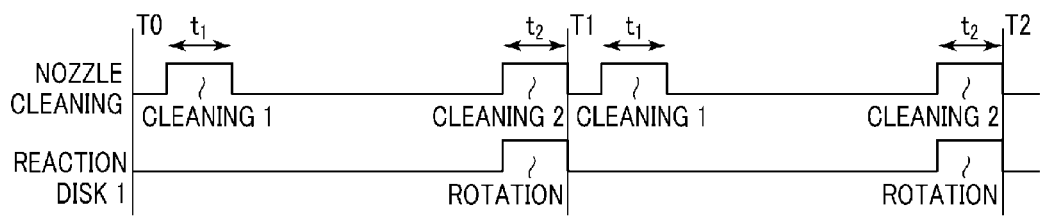
FIG. 4 is a drawing showing a case where two cleaning cycles each including two nozzle cleaning periods are set in an embodiment of the present invention.

FIG. 4 is a drawing showing a case where two cleaning cycles each including two nozzle cleaning periods (the first cleaning period and the last cleaning period in one cycle in FIG. 3) are set in an embodiment of the present invention.

A nozzle cleaning method in a case where the nozzle cleaning timing shown in FIG. 4 has been set will be explained below as an embodiment of the present invention.

FIG. 5 is a drawing showing a cleaning method for the nozzle 11a in a case where the nozzle 11a performs the sample suction once from one sample as an embodiment of the present invention. In the example shown in FIG. 5, a threshold value is set at 20 μL. When the sample suction quantity of the nozzle is less than 20 μL, the sample suction, the sample discharge and the nozzle cleaning are performed in one operation cycle. When the sample suction quantity of the nozzle is 20 μL or more, the sample suction and the sample discharge are performed in one operation cycle and two nozzle cleaning processes (CLEANING 1, CLEANING 2) are performed in the next cycle.

In the example of FIGS. 1, 2 and 5, in one operation cycle from time T0 to time T1, the sample dispensation mechanism 11 accesses a sample vessel 15 (that has been set on the rack 16 on the sample transfer mechanism 17) that is situated at the sample suction position 15w, and performs the sample suction for a relatively small amount (e.g., 6 μL) with the sample nozzle 11a. Subsequently, the sample dispensation mechanism 11 accesses a reaction vessel 2 on the reaction disk 1 and performs the sample discharge for 1 μL, for example.

After the completion of the sample discharge, the nozzle 11a is moved by the sample dispensation mechanism 11 into the cleaning bath 13. In the cleaning bath 13, the outer surface and the inner surface of the nozzle 11a are cleaned by opening the solenoid valves 52 and 58 in the time "CLEANING 2" shown in FIG. 4.

In the next cycle from time T1 to time T2, the sample dispensation mechanism 11 accesses a new sample vessel 15 that has been set on the rack 16 on the sample transfer mechanism 17 and performs the sample suction for a relatively large amount (e.g., 30 μL) with the sample nozzle 11a. Subsequently, the sample dispensation mechanism 11 accesses a reaction vessel 2 on the reaction disk 1 and performs the sample discharge for 25 μL, for example.

After the completion of the sample discharge, the nozzle 11a is moved by the sample dispensation mechanism 11 into the cleaning bath 13.

In the next cycle from time T2 to time T3, the outer surface and the inner surface of the nozzle 11a are cleaned by opening the solenoid valves 52 and 58 in the times "CLEANING 1" and "CLEANING 2" shown in FIG. 4.

In the above example, the control of the cycles to be used for the cleaning and the number of times of cleaning is made possible by referring to the values 6 μL and 30 μL as a track record of the sample suction quantity and setting the threshold value at 20 μL. Incidentally, it is either possible to set one threshold value or to set multiple threshold values.

FIGS. 6(a)-6(e) are diagrams for explaining the operation in a case where two threshold values are set (e.g., a second threshold value is set at 35 μL in addition to the first threshold value). FIGS. 6(a)-6(e) shows multiple examples of the cleaning method in cases where the nozzle 11a performs the sample suction for 40 μL, for example. In these examples, when the sample suction quantity of the nozzle 11a is the second threshold value or more, the cleaning is performed three or four times in the two cycles subsequent to the cycle in which the sample suction and the sample discharge were performed.

In the example of FIG. 6(a), the CLEANING 1 and the CLEANING 2 are performed in the cycle T1-T2 (i.e., cycle from time T1 to time T2, ditto for other cycles) after the cycle T0-T1, and the CLEANING 1 is performed in the next cycle T2-T3.

In the example of FIG. 6(b), the CLEANING 1 and the CLEANING 2 are performed in the cycle T1-T2 after the cycle T0-T1, and the CLEANING 2 is performed in the next cycle T2-T3.

In the example of FIG. 6(c), the CLEANING 1 and the CLEANING 2 are performed in the cycle T1-T2 after the cycle T0-T1, and the CLEANING 1 and the CLEANING 2 are performed in the next cycle T2-T3.

In the example of FIG. 6(d), the CLEANING 1 is performed in the cycle T1-T2 after the cycle T0-T1, and the CLEANING 1 and the CLEANING 2 are performed in the next cycle T2-T3.

In the example of FIG. 6(e), the CLEANING 2 is performed in the cycle T1-T2 after the cycle T0-T1, and the CLEANING 1 and the CLEANING 2 are performed in the next cycle T2-T3.

By setting multiple times of cleaning and multiple cleaning cycles when the suction quantity of the nozzle 11a is the second threshold value or more as in the examples shown in FIGS. 6(a) and 6(b), the cleaning of the nozzle 11a can be performed with appropriate timing and appropriate amounts of cleaning water. Further, by employing the multi-cycle operation performing the sample suction and the sample discharge in the first cycle and performing the cleaning in the second and subsequent cycles when the sample suction quantity is large, an appropriate cleaning operation can be executed based on the track record of the sample suction quantity.

Next, a nozzle cleaning method in a case where the nozzle 11a performs the sample suction multiple times from one sample will be explained below as another embodiment of the present invention.

FIGS. 7-10 are drawings for explaining cases where the sample suction is performed multiple times from one sample. A value 20 μL is set as the threshold value of the sample suction quantity. When the sample suction quantity is less than 20 μL, the sample dispensation and the cleaning operation are performed in the cycle T0-T1 (one cycle in FIG. 5). When the sample suction quantity is 20 μL or more, the sample dispensation and is performed in the cycle T1-T2 in FIG. 5 and the cleaning operation is performed in the cycle T2-T3.

FIG. 7 is a drawing showing an example in which 6 μL of sample suction and 1 μL of sample discharge, for example, were performed in one cycle T0-T1 and thereafter 1 μL of sample suction and 1 μL of sample discharge were performed from one sample in the next cycle T1-T2.

In the example shown in FIG. 7, the track record of the sample suction quantity indicates that the first sample suction was performed for 6 μL, thereafter 1 μL of the sample was discharged to the reaction vessel 2, and 1 μL of the sample was sucked in in the second sample suction. Therefore, the remaining amount of the sample in the nozzle 11a is 1 μL+5 μL=6 μL. Since the sample suction quantities in the two times of sample suction are both below the threshold value 20 μL, the dispensation and cleaning operation shown in the cycle T0-T1 in FIG. 5 is performed in the first cycle and the NOZZLE CLEANING 2 is performed in the second sample suction discharge cycle T1-T2.

When the suction track records made by the first sample suction and the second sample suction are the threshold value 20 μL or more, the dispensation and cleaning operation shown in the cycles T1-T3 (cycle T1-T2 and cycle T2-T3) in FIG. 5 is performed.

FIG. 8 shows an example in which 20 μL of sample suction and 15 μL of sample discharge, for example, were performed in the cycle T0-T1 and thereafter 15 μL of sample suction and 15 μL of sample discharge were performed from one sample in the cycle T1-T2. In this case, the track record of the suction quantity indicates that the first sample suction was performed for 20 μL, thereafter 15 μL of the sample was discharged to the reaction vessel 2, and 15 μL of the sample was sucked in in the second sample suction. Therefore, the remaining amount of the sample in the nozzle 11a is 15 μL+5 μL=20 μL. Since the sample suction quantity is over the threshold value 20 μL both in the first sample suction and the second sample suction, the cleaning is performed according to the cleaning operation shown in the cycles T1-T3 in FIG. 5.

Since the above example of FIG. 8 is an example of 2-cycle dispensation which is separated into a dispensation cycle and a cleaning cycle in cases of sample suction for 20 μL or more, the cleaning is omitted in the first dispensation cycle and in the subsequent dispensation cycle in FIG. 8 and two cleaning processes are performed in the third cycle. Consequently, the second dispensation cycle is performed between time T1 and time T2, the cleaning is performed in the cycle T2-T3, and the whole process from the dispensation to the cleaning is finished in three cycles. Since the dispensation cycles and the cleaning cycle are set as separate cycles, it becomes possible to shorten the time of each cycle (time per cycle).

FIG. 9 shows an example in which 6 μL of sample suction and 1 μL of sample discharge, for example, were performed in the cycle T0-T1 and thereafter 15 μL of sample suction and 15 μL of sample discharge were performed from one sample in the cycle T1-T2. In this case, the track record of the suction quantity indicates that the first sample suction was performed for 6 μL, thereafter 1 μL of the sample was discharged to the reaction vessel 2, and 15 μL of the sample was sucked in in the second sample suction. Therefore, the remaining amount of the sample in the nozzle 11a is 15 μL+5 μL=20 μL. Since the suction quantity in the second sample suction is over the threshold value 20 μL, two cleaning processes (CLEANING 1 and CLEANING 2) are performed in the cycle T2-T3 according to the cleaning operation shown in the cycle T2-T3 in FIG. 5.

FIG. 10 shows an example in which 20 μL of sample suction and 15 μL of sample discharge, for example, were performed in the cycle T0-T1 and thereafter 1 μL of sample suction and 1 μL of sample discharge were performed from one sample in the cycle T1-T2. In this case, the track record of the suction quantity indicates that the first sample suction was performed for 20 μL, thereafter 15 μL of the sample was discharged to the reaction vessel 2, and 1 μL of the sample was sucked in in the second sample suction. Therefore, the remaining amount of the sample in the nozzle 11a is 1 μL+5 μL=6 μL. Since the suction quantity in the first sample suction is the threshold value 20 μL or more, the cleaning is performed according to the cleaning operation shown in the cycle T2-T3 in FIG. 5.

Similarly to the case of FIG. 8, cleaning in the dispensation cycles is omitted and the cleaning is performed in a separate cycle. Consequently, the second dispensation cycle is performed between time T1 and time T2, the cleaning is performed in the cycle T2-T3, and the whole process from the dispensation to the cleaning is finished in three cycles. Therefore, it becomes possible also in this case to shorten the cycle time (time per cycle).

Further, in the example of FIG. 10, the sample suction quantity in the second dispensation cycle T1-T2 is 6 μL (indicating a short sample suction time), and thus one nozzle cleaning process is possible in the second dispensation cycle T1-T2.

Accordingly, the two cleaning processes may also be separately arranged in the cycle T1-T2 and the cycle T2-T3 as in the examples shown in FIGS. 11(a)-11(b). FIG. 11(a) shows an example of performing the CLEANING 2 in the cycle T1-T2 and performing the CLEANING 2 also in the cycle T2-T3. FIG. 11(b) shows an example of performing the CLEANING 2 in the cycle T1-T2 and performing the CLEANING 1 in the cycle T2-T3.

By preventing interference between the sample dispensation mechanism and other dispensation mechanisms and securing a cleaning interval, when stains remain in the system water (which replaced the sample in the first cleaning process) in the nozzle 11a, a sufficient time for the diffusion of the stains into the system water can be gained and more efficient nozzle cleaning can be performed in the second cleaning process.

When the sample suction is performed three or more times from one sample, the number of times and the timing of the nozzle cleaning are determined by performing the threshold value judgment regarding the maximum sample suction quantity of the first and second suction processes and the sample suction quantity of the third suction process. When the sample suction is performed four or more times from one sample, the number of times and the timing of the nozzle cleaning are determined by performing the threshold value judgment regarding the maximum sample suction quantity of the first through third suction processes and the sample suction quantity of the fourth suction process. To sum up, as shown in FIGS. 7-11, when the sample suction is performed N times (N: integer larger than 1) from one sample, the nozzle cleaning is carried out efficiently by determining the number of times and the timing of the nozzle cleaning based on the maximum sample suction quantity of the first through (N−1)-th suction processes and the sample suction quantity of the N-th suction process immediately before the nozzle cleaning without unnecessarily increasing the number of operation cycles. While two types of nozzle cleaning patterns (FIG. 7 and FIGS. 8-10) have been shown in FIGS. 7-11, it is possible in FIGS. 8-10 to employ four types of nozzle cleaning patterns by changing the cleaning timing as in FIGS. 11(a)-11(b).

Further, the whole sample dispensation process is separated into one or more dispensation cycles (including no cleaning operation) and a cleaning cycle as in the examples shown in FIGS. 8, 9 and 10. In this case, the shortening of the cycle time (time of one cycle) becomes possible.

When the sample suction quantity of the nozzle is small, sufficient cleaning of the nozzle is possible just by performing the cleaning for a short time. Since the sample dispensation time is also short, the cleaning operation is performed in a sample dispensation cycle. When the sample suction quantity of the nozzle is large, a cleaning cycle separate from the sample dispensation cycle(s) is set in order to ensure the sufficient cleaning of the nozzle.

This makes it possible to secure an appropriate nozzle cleaning time and suppress the deterioration in the accuracy of the analysis even in cases where the operation cycle time (the time of one operation cycle) is shortened to speed up the processing of the sample.

Figure 12:
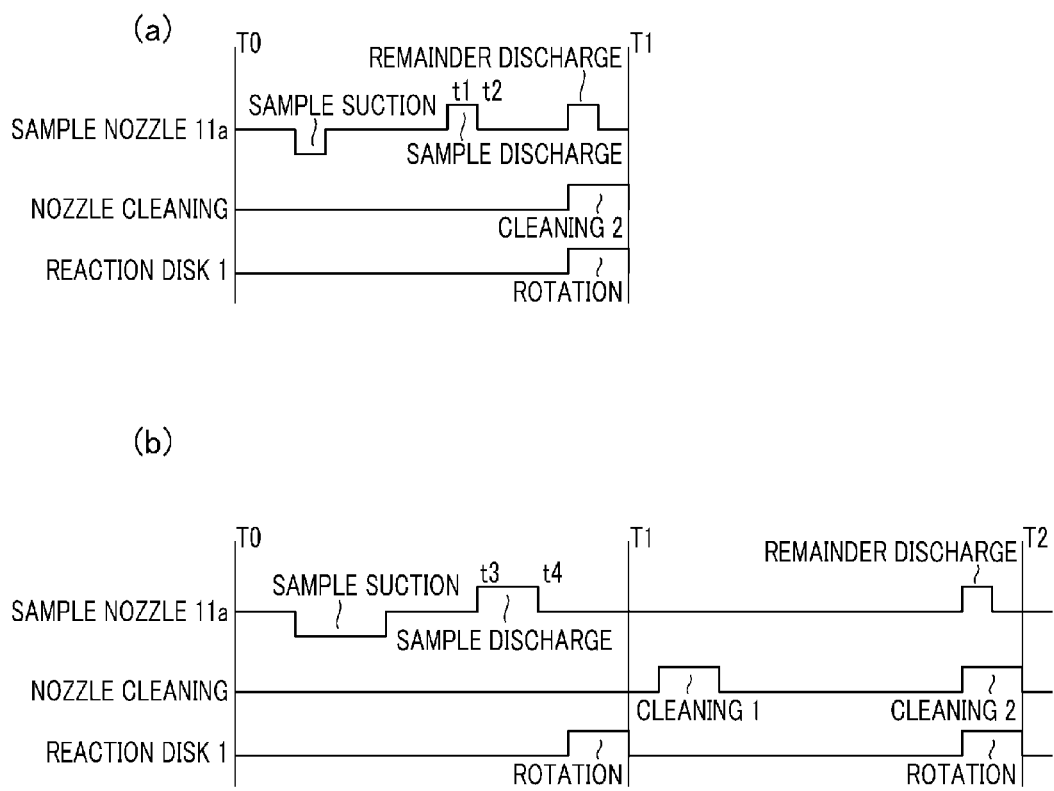
FIGS. 12(a)-12(b) are diagrams for explaining a modification of the first embodiment of the present invention.

FIGS. 12(a)-12(b) are diagrams for explaining a modification of the first embodiment of the present invention. FIG. 12(a) shows an example in which the threshold value is assumed to be 20 μL, the nozzle 11a performs the sample suction for a relatively small amount (e.g., 6 μL), accesses a reaction vessel 2 on the reaction disk 1 and performs the sample discharge for 1 μL, for example, and the CLEANING 2 is performed in the cycle.

FIG. 12(b) shows an example in which the threshold value is assumed to be 20 μL, the nozzle 11a performs the sample suction for a relatively large amount (e.g., 30 μL), accesses a reaction vessel 2 on the reaction disk 1 and performs the sample discharge for 25 μL, for example, and the CLEANING 1 and the CLEANING 2 are performed in the next cycle.

The sample discharge start time $t_1$ and the sample discharge end time $t_2$ in the sample dispensation cycle in the example of FIG. 12(a) represent timing that has been set according to the sample suction quantity. Similarly, the sample discharge start time $t_3$ and the sample discharge end time $t_4$ in the sample dispensation cycle in the example of FIG. 12(b) represent timing that has been set according to the sample suction quantity.

In short, the sample discharge start timing and the sample discharge end timing are set variably according to the sample suction quantity.

The variable setting of the sample discharge start timing and the sample discharge end timing according to the sample suction quantity (as in the examples in FIG. 12(a)-12(b)) also makes it possible to secure an appropriate nozzle cleaning time and to suppress the deterioration in the accuracy of the analysis even in cases where the operation cycle time (the time of one operation cycle) is shortened to speed up the processing of the sample.

Figure 13:
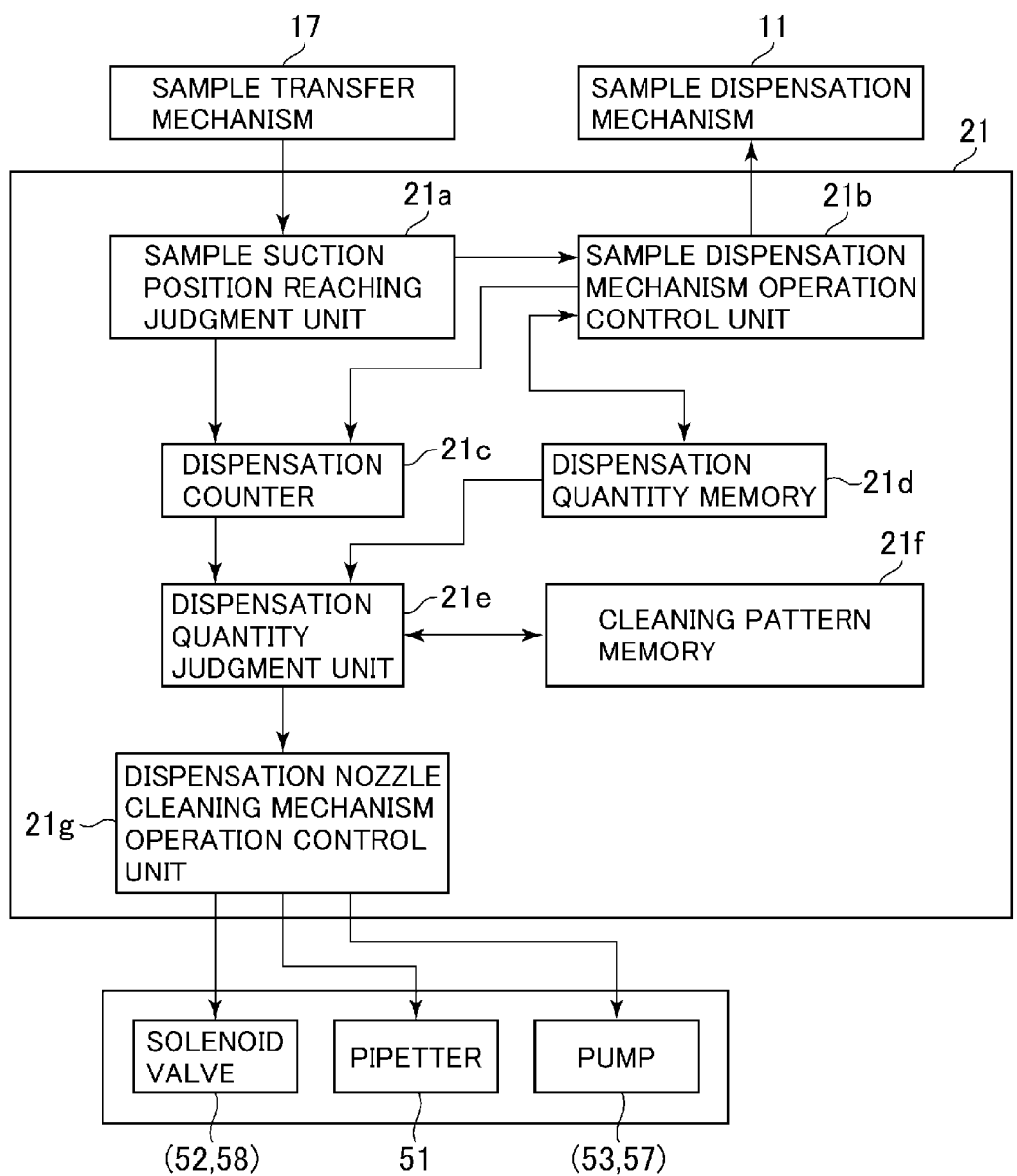
FIG. 13 is a block diagram showing the operation and functional blocks of a controller in the first embodiment of the present invention.
Figure 14:
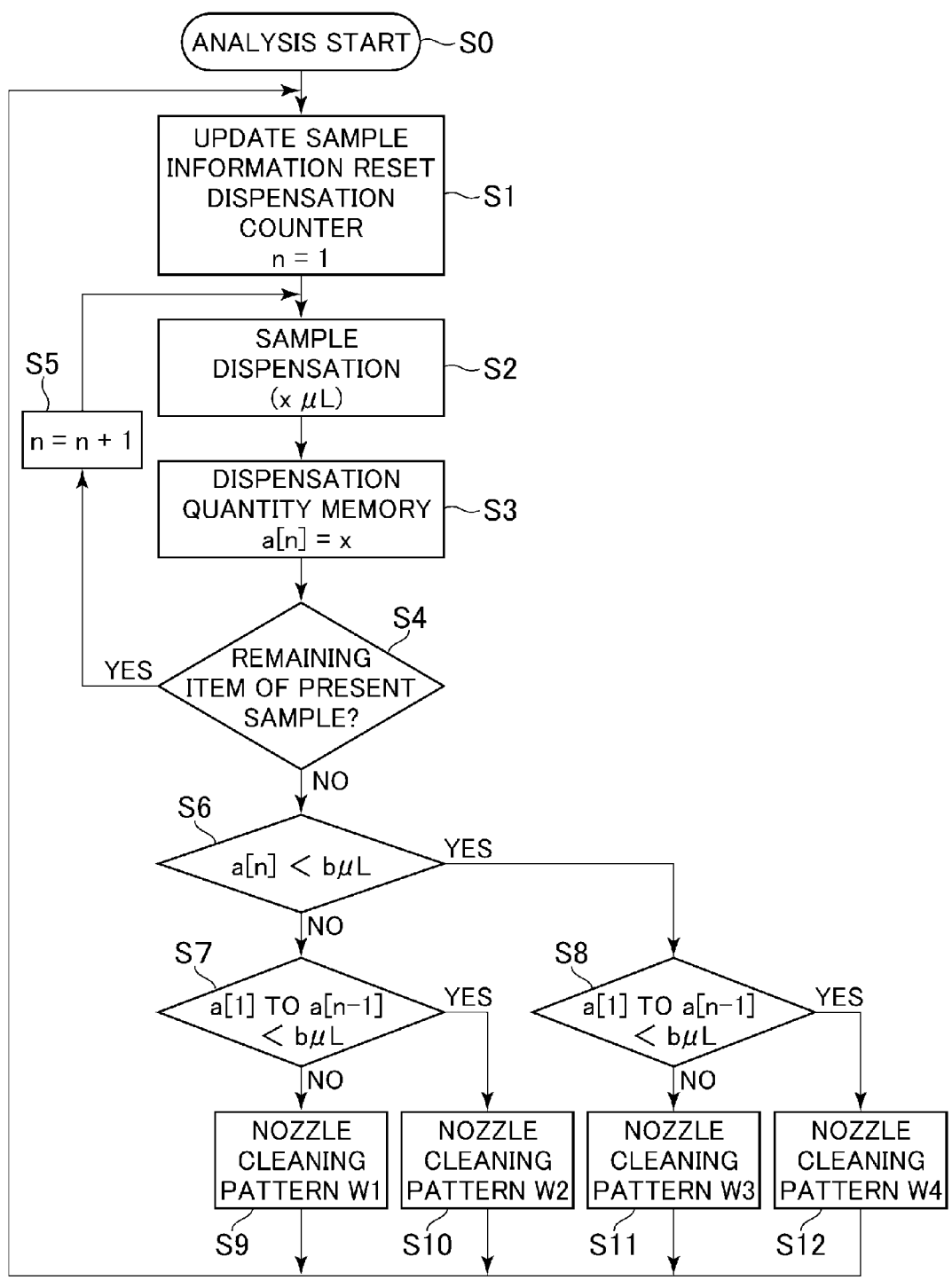
FIG. 14 is an operation flow chart in the first embodiment of the present invention.

FIG. 13 is a block diagram showing the operation and functional blocks of the controller 21 for performing the nozzle cleaning operation in the above-described first embodiment of the present invention. FIG. 14 is an operation flow chart.

In FIG. 13, the controller 21 includes a sample suction position reaching judgment unit 21a, a sample dispensation mechanism operation control unit 21b, a dispensation counter 21c, a dispensation quantity memory 21d, a dispensation quantity judgment unit 21e, a cleaning pattern memory 21f, and a dispensation nozzle cleaning mechanism operation control unit 21g.

Next, the nozzle cleaning operation will be explained below by referring to FIGS. 13 and 14.

When the sample suction position reaching judgment unit 21a judges that the sample vessel 15 has reached the sample suction position 15w after the analysis start (step S0) in FIG. 14, sample information is updated and the dispensation counter 21c is reset to n=1 (step S1).

Under the control by the sample dispensation mechanism operation control unit 21b, the sample dispensation mechanism 11 accesses the sample vessel 15, pipettes the sample with the sample nozzle 11a, accesses a reaction vessel 2 on the reaction disk 1, and performs the sample dispensation for x μL (step S2). Dispensation information on the dispensation quantity x μL of the sample is stored in an array a[i] of the dispensation quantity memory 21d as a[n]=x μL (step S3). The sample dispensation mechanism operation control unit 21b judges whether or not there is a remaining analysis item of the sample stored in the same sample vessel 15 (step S4). If there is a remaining analysis item, the nozzle cleaning for the sample nozzle 11a is canceled and the dispensation counter 21c is updated according to the following expression (1) (step S5):

$$n=n+1 \qquad (1)$$

After the update of the dispensation counter 21c, the process returns to step S2. In the next cycle, the sample dispensation mechanism 11 accesses the sample vessel 15, pipettes the sample with the sample nozzle 11a, accesses a reaction vessel 2, performs the sample dispensation, and stores the dispensation quantity in the array a[i] of the dispensation quantity memory 21d (step S3).

Subsequently, the sample dispensation mechanism operation control unit 21b judges whether or not there is a remaining analysis item of the sample stored in the same sample vessel 15 (step S4). If no remaining analysis item is judged to exist, the dispensation quantity judgment unit 21e makes a judgment on whether the sample dispensation quantity a[n] of the n-th sample dispensation is less than a certain dispensation quantity threshold value (e.g., b μL) or not (step S6).

If the sample dispensation quantity a[n] of the n-th sample dispensation is less than the dispensation quantity threshold value b μL in the step S6, the process advances to step S8. The dispensation quantity judgment unit 21e judges whether or not all the sample dispensation quantities a[1]-a[n−1] of the first through (n−1)-th sample dispensations are less than the dispensation quantity threshold value b μL (step S8). This judgment is equivalent to judging whether the maximum sample dispensation quantity among the sample dispensation quantities a[1]-a[n−1] is less than the dispensation quantity threshold value b μL or not.

If all the sample dispensation quantities a[1]-a[n−1] are judged in the step S8 to be less than the dispensation quantity threshold value b μL, a cleaning pattern W4 stored in the cleaning pattern memory 21f (e.g., the cleaning pattern in the cycle T0-T1 in FIG. 5) is selected (step S12). The operation of the cleaning mechanism (the solenoid valves 52 and 58, the pipetter 51, the pumps 53 and 57) is controlled to suit the cleaning pattern W4 by the dispensation nozzle cleaning mechanism operation control unit 21g.

If it is judged in the step S8 that any one of the sample dispensation quantities a[1]-a[n−1] is the dispensation quantity threshold value b μL or more, that is, the maximum sample suction quantity among the sample dispensation quantities a[1]-a[n−1] is the dispensation quantity threshold value b μL or more, a cleaning pattern W3 stored in the cleaning pattern memory 21f (e.g., the cleaning pattern in the cycles from time T1 to time T3 in FIGS. 11(a)-11(b)) is selected (step S11) and the operation of the cleaning mechanism is controlled to suit the cleaning pattern W3 by the dispensation nozzle cleaning mechanism operation control unit 21g.

If the sample dispensation quantity a[n] of the n-th sample dispensation is the dispensation quantity threshold value b μL or more in the step S6, the process advances to step S7. The dispensation quantity judgment unit 21e judges whether or not all the sample dispensation quantities a[1]-a[n−1] of the first through (n−1)-th sample dispensations are less than the dispensation quantity threshold value b μL (step S7).

If all the sample dispensation quantities a[1]-a[n−1] are judged in the step S7 to be less than the dispensation quantity threshold value b μL, a cleaning pattern W2 stored in the cleaning pattern memory 21f (e.g., the cleaning pattern in the cycles from time T1 to time T3 in FIG. 5) is selected (step S10). The operation of the cleaning mechanism (the solenoid valves 52 and 58, the pipetter 51, the pumps 53 and 57) is controlled to suit the cleaning pattern W2 by the dispensation nozzle cleaning mechanism operation control unit 21g.

If it is judged in the step S7 that any one of the sample dispensation quantities a[1]-a[n−1] is the dispensation quantity threshold value b μL or more, a cleaning pattern W1 stored in the cleaning pattern memory 21f (e.g., the cleaning pattern in the cycles from time T1 to time T3 in FIG. 6(c)) is selected (step S9) and the operation of the cleaning mechanism is controlled to suit the cleaning pattern W1 by the dispensation nozzle cleaning mechanism operation control unit 21g.

As described above, in the first embodiment of the present invention, idle time and the level of contamination (contamination level) of the nozzle 11a in the cycle after the n-th dispensation are judged by making the dispensation quantity threshold value judgment on the n-th dispensation quantity. Further, the contamination level of the nozzle 11a before the n-th dispensation is judged by making the dispensation quantity threshold value judgment for the first through (n−1)-th dispensations. Accordingly, optimum nozzle cleaning can be carried out based on the contamination level of the nozzle 11a and the idle time after the dispensation.

Therefore, it is possible to implement an automatic analyzer capable of ensuring sufficient nozzle cleaning and suppressing the deterioration in the accuracy of the analysis even when the processing of the sample is speeded up.

The selection from the nozzle cleaning patterns W1-W4 by the steps S6-S8 has been explained above referring to FIG. 14. While an example in which the nozzle cleaning patterns W1-W4 are different from one another (no two patterns selected from the nozzle cleaning patterns W1-W4 are the same) was used for the explanation, the present invention is not restricted by such a strict condition that no two patterns selected from the nozzle cleaning patterns W1-W4 are the same. For example, the nozzle cleaning patterns W2 and W3 may be the same cleaning patterns. Further, the nozzle cleaning patterns W1-W3 may be the same cleaning patterns as in FIGS. 7-10. It is sufficient if the nozzle cleaning patterns W1-W4 include at least two types of nozzle cleaning patterns. Suppose the nozzle cleaning patterns W1-W4 include two types of nozzle cleaning patterns, it is desirable if the two different types of nozzle cleaning patterns are the nozzle cleaning patterns W1-W3 and the nozzle cleaning pattern W4 since there is a major difference between the two types in that the nozzle cleaning pattern W4 does not include a sample suction quantity that is the dispensation quantity threshold value b μL or more and the nozzle cleaning patterns W1-W3 include at least a sample suction quantity that is the dispensation quantity threshold value b μL or more.

Second Embodiment

Figure 15:
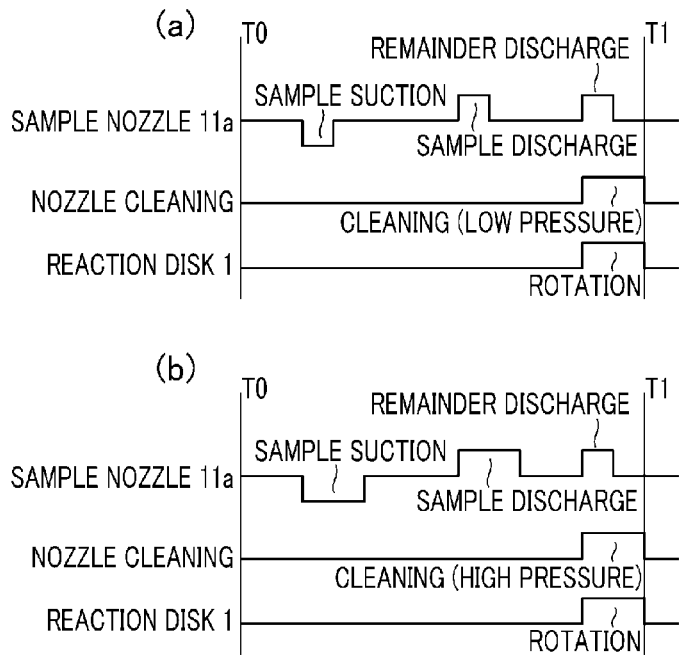
FIGS. 15(a)-15(b) are diagrams for explaining the operation of a second embodiment of the present invention.
Figure 16:
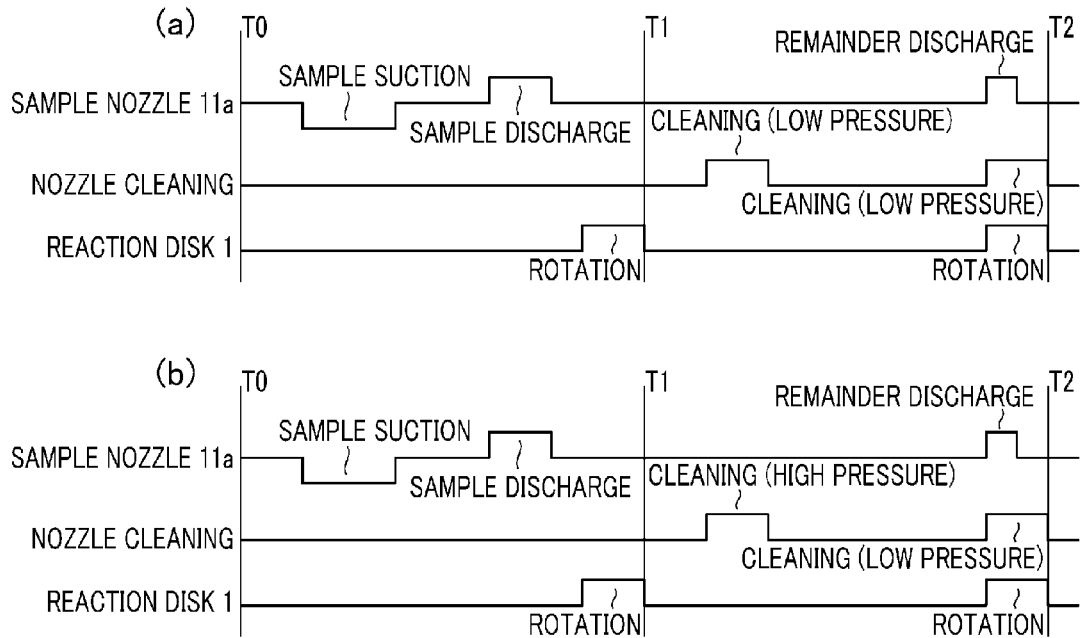
FIGS. 16(a)-16(b) are diagrams for explaining the operation of the second embodiment of the present invention.

Next, a second embodiment of the present invention will be described below by referring to FIGS. 15 and 16.

FIGS. 15(a)-(b) and 16(a)-(b) are drawings for explaining the operation of the second embodiment of the present invention. The second embodiment is an example in which the threshold value of the sample suction quantity of the nozzle 11a is set at 20 μL and the cleaning operation for the nozzle 11a is changed based on the track record of the sample suction quantity of the nozzle 11a.

Incidentally, the overall configuration of the automatic analyzer and the configuration of the dispensation mechanism, etc. in the second embodiment are equivalent to those in the first embodiment.

While the number of times of cleaning and the cleaning timing are adjusted based on the track record of the sample suction quantity of the nozzle 11a in the first embodiment, cleaning pressure, the number of times of cleaning and the cleaning timing are adjusted in the second embodiment based on the track record of the sample suction quantity of the nozzle 11a.

FIG. 15(a) is a drawing showing a case where the nozzle 11a performed 6 μL of sample suction and 1 μL of sample discharge from one sample, for example. In the example shown in FIG. 15(a), the track record of the sample suction quantity of the nozzle 11a is 6 μL, which is below the threshold value 20 μL. Therefore, the sample dispensation and the cleaning of the nozzle 11a (with the pressure of the pump 53 set at a low pressure (e.g., 200 kPa)) are performed in the period T0-T1.

FIG. 15(b) shows a case where the nozzle 11a performed 20 μL of sample suction and 15 μL of sample discharge from one sample, for example. In the example shown in FIG. 15(b), the track record of the suction quantity is 20 μL, which is the threshold value 20 μL or more. Therefore, the sample dispensation and the cleaning of the nozzle 11a (with the pressure of the pump 53 set at a high pressure (e.g., 400 kPa)) are performed in the period T0-T1.

Since the cleaning efficacy changes proportionally to the square root of the cleaning pressure of the nozzle 11a, approximately 1.4 times of the original cleaning efficacy of the nozzle 11a can be achieved in the same cleaning time in the above example. Accordingly, optimum nozzle cleaning suitable for the sample suction quantity of the nozzle 11a can be performed without the need of increasing the number of operation cycles.

FIGS. 16(a)-16(b) are diagrams for explaining the operation of another example of the second embodiment of the present invention.

FIGS. 16(a)-16(b) show an example in which a first threshold value is set at 20 μL and a second threshold value is set at 35 μL, for example. When the sample suction quantity of the nozzle 11a is less than 20 μL, the cleaning operation shown in FIG. 15(a) is carried out.

In FIG. 16(a), when the nozzle 11a performed the sample suction for 30 μL, for example, the sample suction quantity is the first threshold value or more and less than the second threshold value. In this case, cleaning with a low pressure (e.g., 200 kPa) is performed twice in the cycle T1-T2 after the cycle T0-T1 in which the sample suction and the sample discharge were performed.

In FIG. 16(b), when the nozzle 11a performed the sample suction for 40 μL, for example, the sample suction quantity is the second threshold value or more. In this case, cleaning with a high pressure (e.g., 400 kPa) and cleaning with a low pressure (e.g., 200 kPa) are performed in the cycle T1-T2 after the cycle T0-T1 in which the sample suction and the sample discharge were performed.

By adjusting the number of times of cleaning, the cleaning cycle and also the cleaning pressure as above, cleaning of the nozzle 11a with appropriate cleaning efficacy can be performed with appropriate timing.

Incidentally, in cases where the sample suction is performed multiple times from the same sample, the number of times and the timing of the sample nozzle cleaning are controlled in the same way as in the first embodiment. Specifically, one of the nozzle cleaning patterns W1-W4 is selected and executed according to the flow chart of FIG. 14.

As described above, effects similar to those of the first embodiment can be achieved also by the second embodiment.

Third Embodiment

Next, a third embodiment of the present invention will be described below by referring to FIGS. 17 and 18.

Figure 17:
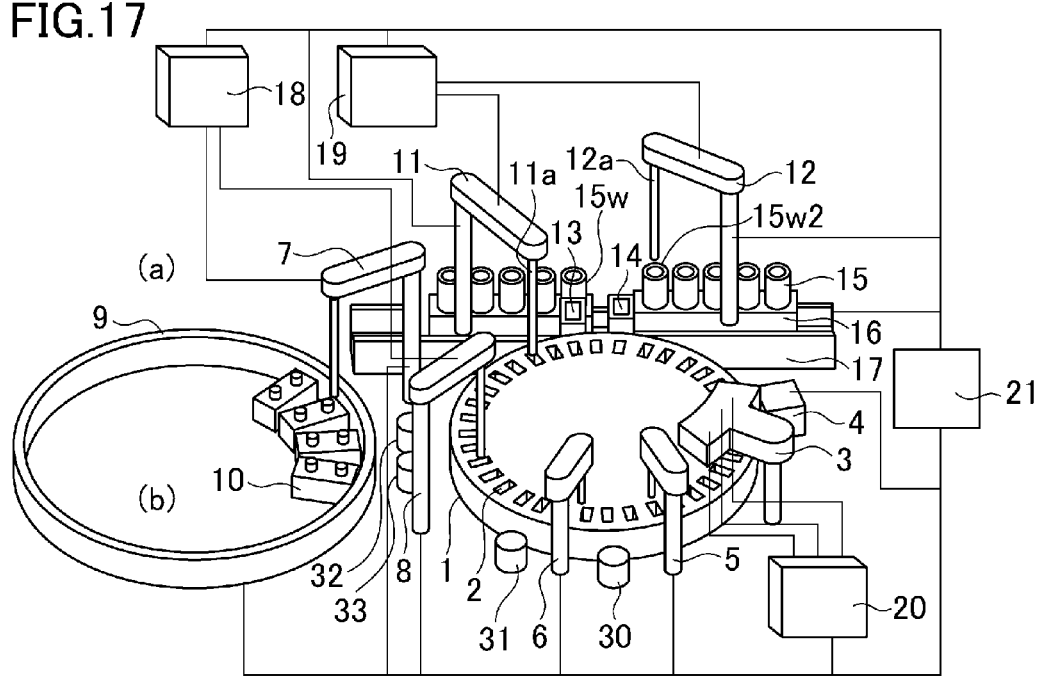
FIG. 17 is a schematic diagram showing the overall configuration of an automatic analyzer to which the present invention is applied.
Figure 18:
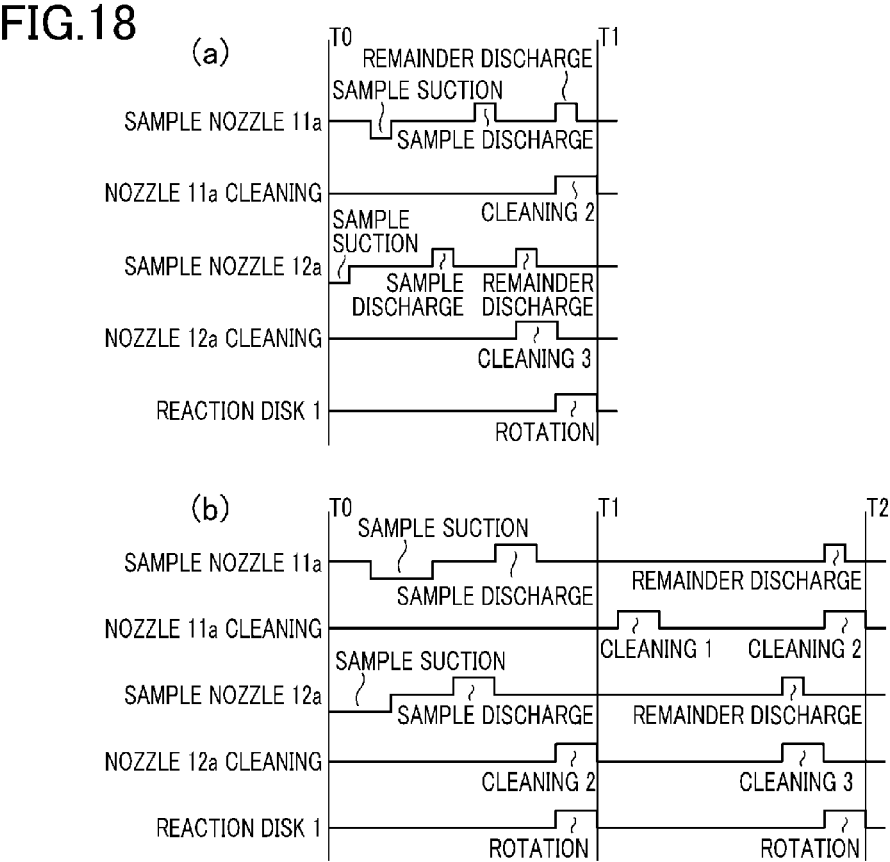
FIGS. 18(a)-18(b) are diagrams for explaining the operation of a third embodiment of the present invention.

FIG. 17 is a schematic diagram showing the overall configuration of an automatic analyzer to which the present invention is applied.

In FIG. 17, the automatic analyzer shown in FIG. 1 (automatic analyzer to which the present invention is applied) is equipped with another sample dispensation mechanism 12. Similarly to the sample dispensation mechanism 11, the sample dispensation mechanism 12 includes a sample nozzle 12a to which the sample pump 19 is connected. The sample nozzle 12a moves along an arc around the rotation axis of the sample dispensation mechanism 12 and performs the sample dispensation by sucking in a sample from a sample vessel 15 situated at a sample suction position 15W2 and discharging the sample to a reaction vessel 2.

FIGS. 18(a)-18(b) are diagrams for explaining the operation of the third embodiment of the present invention. The third embodiment is an example in which the sample suction quantity threshold values of the nozzles 11a and 12a are set at 20 μL and the cleaning operation of the nozzles 11a and 12a is changed based on the track record of the sample suction quantities of the nozzles 11a and 12a.

In FIGS. 18(a)-18(b), there are three cleaning times in total in regard to the cleaning timing: the first cleaning time and the last two cleaning times in one cycle in FIG. 3.

FIG. 18(a) is a drawing showing a case where each nozzle 11a, 12a performed 6 μL of sample suction and 1 μL of sample discharge from one sample, for example. In the example shown in FIG. 18(a), the track records of the sample suction quantities of the nozzles 11a and 12a are 6 μL, which is below the threshold value 20 μL. In this case, the sample dispensation and the cleaning are performed in the cycle T0-T1, in which the nozzle 11a performs the cleaning in the time "CLEANING 2" and the nozzle 12a performs the cleaning in the time "CLEANING 3".

FIG. 18(b) is a drawing showing a case where each nozzle 11a, 12a performed 30 μL of sample suction and 25 μL of sample discharge from one sample, for example. In the example shown in FIG. 18(b), the track records of the sample suction quantities of the nozzles 11a and 12a are 30 μL, which is above the threshold value 20 μL. In this case, the nozzle 11a performs the sample dispensation in the cycle T0-T1 and performs the cleaning in the times "CLEANING 1" and "CLEANING 2" in the cycle T1-T2. The nozzle 12a performs the sample dispensation and the first cleaning (in the time "CLEANING 2") in the cycle T0-T1 and performs the second cleaning in the time "CLEANING 3" in the cycle T1-T2.

Also in such an automatic analyzer comprising two or more sample nozzles, cleaning interference between the sample nozzles 11a and 12a can be avoided without increasing the number of cleaning cycles as explained above. Especially, by the avoidance of the cleaning interference, the cleaning can be carried out without causing deterioration in the cleaning power (drop in the discharge pressure of the cleaning liquid from each nozzle) even in cases where the same pump is used for supplying the cleaning liquid for the cleaning of the sample nozzle 11a and the cleaning liquid for the cleaning of the sample nozzle 12a. This is because simultaneous discharge of the cleaning liquid from the two nozzles never occurs and dispersion of the discharge pressure can be suppressed. For example, the avoidance of the cleaning interference can be realized by closing the cleaning liquid supply valve for one nozzle just before supplying the cleaning liquid to the other nozzle. In the example of FIGS. 18(a)-18(b), the deterioration in the cleaning power can be suppressed by switching the state from the closure of the cleaning liquid supply valve for the nozzle 11a to the closure of the cleaning liquid supply valve for the nozzle 12a between the "CLEANING 3" and the "CLEANING 2", for example.

Incidentally, in cases where the sample suction is performed multiple times from the same sample, the number of times and the timing of the cleaning of the sample nozzle are controlled in the same way as in the first embodiment. Specifically, one of the nozzle cleaning patterns W1-W4 is selected and executed according to the flow chart of FIG. 14.

As described above, effects similar to those of the first embodiment can be achieved also by the third embodiment.

DESCRIPTION OF REFERENCE CHARACTERS 1 reaction disk
2 reaction vessel
3 cleaning mechanism
4 spectrophotometer
5, 6 stirring mechanism
7, 8 reagent dispensation mechanism
9 reagent disk
10 reagent bottle
11 sample dispensation mechanism
11a sample nozzle
12 sample dispensation mechanism
12a sample nozzle
13 cleaning bath
14 cleaning bath
15 sample vessel
15w sample suction position
15w2 sample suction position
16 rack
17 sample transfer mechanism
18 reagent pump
19 sample pump
20 cleaning pump
21 controller
21a sample suction position reaching judgment unit
21b sample dispensation mechanism operation control unit
21c dispensation counter
21d dispensation quantity memory
21e dispensation quantity judgment unit
21f cleaning pattern memory
21g dispensation nozzle cleaning mechanism operation control unit
30 cleaning bath
31, 32, 33 cleaning bath
51 pipetter
52, 58 solenoid valve
53, 57 pump 54 tank
55 arm

The invention claimed is:

1. An automatic analyzer comprising:
a sample dispensation mechanism including a sample nozzle which sucks in a sample stored in a sample vessel and discharges the sample into a reaction vessel of a plurality of reaction vessels;
a reagent dispensation mechanism which sucks in a reagent stored in a reagent vessel and discharges the reagent into the reaction vessel;
a reaction disk holding the plurality of reaction vessels;
a cleaning bath, including a solenoid valve and a pump, which cleans the sample nozzle with cleaning water;
a photometer which analyzes the sample in the reaction vessel; and
a controller which controls the operation of the reaction disk, sample dispensation mechanism, the reagent dispensation mechanism, the cleaning bath and the photometer,
wherein the controller is programmed to:
control the sample dispensation mechanism to suction a sample stored in a sample vessel in a suction operation, discharge the sample into a reaction vessel in a discharge operation, control the solenoid valve to open and close and control the pump to pump cleaning water thereby cleaning the sample nozzle in a cleaning operation, wherein within repeating and consecutive operation cycles, wherein an operation cycle is a first period of time in which the reaction disk rotates by a first amount, at least one of the suction operation, discharge operation, and cleaning operation are performed within each operation cycle,
for a sample stored in a sample vessel, control the sample dispensation mechanism to perform N number of suction operations to suction the sample N times in different operation cycles, wherein N is an integer greater than 1,
determine whether a maximum sample suction quantity among the first through (N−1) suction operations performed for the sample is greater than a threshold and determine whether a sample suction quantity of the last suction operation among the N number of suction operations for the sample is greater than or equal to the threshold,
if the maximum sample suction quantity and the sample suction quantity of the last suction operation are less than the threshold, perform the cleaning operation of cleaning the sample nozzle once in a same operation cycle in which both the last suction operation was performed and a discharge operation of discharging the sample suctioned by the last suction operation is performed, and
if the sample suction quantity of the last suction operation is greater than or equal to the threshold, perform the cleaning operation of cleaning the sample nozzle at least twice in an operation cycle immediately following an operation cycle in which both the last suction operation was performed and the discharge operation of discharging the sample suctioned by the last suction operation is performed.

2. The automatic analyzer according to claim 1, wherein if the sample suction quantity of the last suction operation of the sample is less than the threshold and the maximum sample suction quantity is greater than or equal to the threshold value, perform the cleaning operation of cleaning the sample nozzle at least twice and one of the at least two cleaning operations is performed in the same operation cycle in which the last suction operation was performed and the discharge operation of discharging the sample suctioned by the last suction operation is performed and the other of the at least two cleaning operations is performed in an operation cycle immediately following.

3. The automatic analyzer according to claim 1, wherein the cleaning bath further includes a pipetter configured to adjust the pressure of water used to clean the sample nozzle, and
wherein the controller is further programmed to:
if all the sample suction quantities of the N number of suction operations are less than a first threshold value, control the pipetter to adjust the water pressure to a first pressure, and
if any of the sample suction quantities of the N number of suction operations is greater than or equal to the threshold, control the pipetter to adjust the water pressure to a second pressure higher than the first pressure.

4. The automatic analyzer according to claim 1, wherein the controller is further programmed to:
if any of the sample suction quantities of the N number of suction operations of the sample are greater than the first threshold and less than a second threshold control the pipetter to adjust the water pressure to the first pressure and perform the cleaning operation twice in the operation cycle subsequent to the operation cycle in which both the last suction operation was performed and the discharge operation of discharging the sample suctioned by the last suction operation is performed, and
if any of the sample suction quantities of the N number of suction operations of the sample are greater than or equal to the second threshold, control the pipetter to adjust the water pressure to a second pressure higher than the first pressure and perform the cleaning operation twice in the operation cycle subsequent to the operation cycle in which both the last suction operation was performed and the discharge operation of discharging the sample suctioned by the last suction operation is performed.

5. The automatic analyzer according to claim 1, wherein the controller is further programmed to:
if the sample suction quantity of the last suction operation is greater than or equal to the threshold and the maximum sample suction quantity is greater than the threshold, perform the cleaning operation of cleaning the sample nozzle four times and two of the four times are performed with an operation cycle immediately following the operation cycle in which both the last suction operation was performed and the discharge operation of discharging the sample suctioned by the last suction operation is performed and perform the other two of the four times in an operation cycle subsequent to the immediately following operation cycle, and
if the sample suction quantity of the last suction operation is greater than or equal to the threshold and the maximum sample suction quantity is less than the threshold, perform the cleaning operation of cleaning the sample nozzle only twice within an operation cycle immediately following the operation cycle in which both the last suction operation was performed and the discharge operation of discharging the sample suctioned by the last suction operation is performed.

* * * * *